(12) United States Patent
Hubbell et al.

(10) Patent No.: US 6,743,521 B2
(45) Date of Patent: Jun. 1, 2004

(54) MULTIFUNCTIONAL POLYMERIC TISSUE COATINGS

(75) Inventors: Jeffrey A. Hubbell, Zumikon (CH); Donald L. Elbert, Zurich (CH); Curtis B. Herbert, Minneapolis, MN (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/403,428

(22) PCT Filed: Apr. 17, 1998

(86) PCT No.: PCT/US98/07590

§ 371 (c)(1),
(2), (4) Date: Jan. 6, 2000

(87) PCT Pub. No.: WO98/47948

PCT Pub. Date: Oct. 29, 1998

(65) Prior Publication Data

US 2003/0087111 A1 May 8, 2003

Related U.S. Application Data

(60) Provisional application No. 60/044,733, filed on Apr. 21, 1997.

(51) Int. Cl.$^7$ ............................ B32B 18/00; B32B 27/06
(52) U.S. Cl. .................... 428/500; 428/411.1; 428/688; 427/2.1; 427/2.12
(58) Field of Search ............................ 428/457, 411.1, 428/500, 688; 525/54.1, 54.2, 54.3; 623/11; 427/2.12, 2.1

(56) References Cited

U.S. PATENT DOCUMENTS

| | | | |
|---|---|---|---|
| 4,289,872 A | 9/1981 | Denkewalter et al. | 528/328 |
| 4,410,688 A | 10/1983 | Denkewalter et al. | 528/328 |
| 5,126,141 A | 6/1992 | Henry | 424/423 |
| 5,573,934 A | 11/1996 | Hubbell et al. | 435/177 |
| 5,578,442 A | * 11/1996 | Desai et al. | 435/1.1 |
| 5,626,863 A | 5/1997 | Hubbell et al. | 424/426 |
| 5,627,233 A | 5/1997 | Hubbell et al. | 525/54.1 |
| 5,714,166 A | 2/1998 | Tomalia et al. | 424/486 |
| 5,849,839 A | * 12/1998 | Hubbell et al. | 525/54.1 |
| 5,908,624 A | 6/1999 | Scott et al. | |
| 6,013,855 A | * 1/2000 | McPherson et al. | 623/11 |
| 6,129,912 A | 10/2000 | Hortin et al. | |
| 6,150,472 A | * 11/2000 | Engbers | 525/404 |
| 6,312,685 B1 | 11/2001 | Fisher et al. | |

FOREIGN PATENT DOCUMENTS

| WO | WO-9318649 A1 | * 9/1993 |
|---|---|---|
| WO | WO 97/28254 A1 | 8/1997 |

OTHER PUBLICATIONS

Aharoni & Murthy, "Spherical non–draining Boc–poly (,$_L$–lysine) macromolecules:SAXS and viscosity studies," *Polymer Communications* 24:132–36 (1983).

Aharoni, et al., "Size and solution properties of globular tert–Butyloxycarbonyl–poly (,$_L$–lysine)," *Macromolecules* 15:1093–98 (1982).

Atassi & Manshouri, "Synthesis of Tolerogenic Monomethoxypolyethylene Glycol and Polyvinyl Alcohol Conjugates of Peptides", *J. Prot. Chem.* 10:623–27 (1991).

Bogdanov, et al., "A new macromolecule as a contrast agent for MR angiography: preparation, properties, and animal studies," *Radiology.* 187(3):701–06 (1993).

Bogdanov, et al., "An adduct of cis–diamminedichloroplatinum(II) and poly(ethylene glycol)poly(L–lysine)–succinate: synthesis and cytotoxic properties," *Bioconjug Chem.* 7(1):144–49 (1996).

Brink, et al., "Using poly(ethylene imine) to graft poly(ethylene glycol) or polysaccharide to polystyrene," *Colloids and Surfaces* 66:149–56 (1992).

Chapman, et al., "Hydraamphiphiles: Novel linear dendritic block copolymer surfactants," *J. Am. Chem. Soc.* 116:11195–96 (1994).

Claesson, et al., "Adsorption and interaction of a graft copolymer of poly(ethylene imine) and poly(ethylene oxide)," *Colloids and Surfaces* 112:131–39 (1996).

Clegg, et al., "Carrier design: Biodistribution of branched polypeptides with a Poly(L–lysine) backbone," *Bioconjug. Chem.* 1:425–30 (1990).

Crescenzi, et al., "Novel types of polysaccharidic assemblies," *Macromol. Chem. Phys.* 196:2873–80 (1995).

Decher & Hong, "Buildup of ultrathin multilayer films by a self–assembly process: II. Consecutive Absorption of anionic and cationic bipolar amphiphiles and polyelectrolytes on charged surface," *Ber. Bunsenges. Phys. Chem.* 95:1430–34 (1991).

Decher, et al., "Proof of multilayer structural organization in self–assembled polycation–polyanion molecular films," *Thin Solid Films* 244:772–77 (1994).

(List continued on next page.)

*Primary Examiner*—Monique R. Jackson
(74) *Attorney, Agent, or Firm*—Holland & Knight LLP

(57) ABSTRACT

Compositions for coating biological and non-biological surfaces, which minimize or prevent cell-cell contact and tissue adhesion, and methods of preparation and use thereof, are disclosed. Embodiments include polyethylene glycol/polylysine (PEG/PLL) block or comb-type copolymers with high molecular weight PLL (greater than 1000, more preferably greater than 100,000); PEG/PLL copolymers in which the PLL is a dendrimer which is attached to one end of the PEG; and multilayer compositions including alternating layers of polycationic and polyanionic materials. The multi-layer polymeric material is formed by the ionic interactions of a polycation and a polyanion. The molecular weights of the individual materials are selected such that the PEG portion of the copolymer inhibits cellular interactions, and the PLL portion adheres well to tissues. The compositions and methods are useful, for example, in inhibiting formation of post-surgical adhesions, protecting damaged blood vessels from thrombosis and restenosis, and decreasing the extent of metastasis of attachment-dependent tumor cells. The compositions and methods are also useful for coating non-biological surfaces such as metallic surfaces.

16 Claims, 3 Drawing Sheets

OTHER PUBLICATIONS

Gitsov, et al., "Novel polyether copolymers consisting of linear and dendritic blocks," *Angew. Chem. Int. Ed. Engl.* 31:1200–02 (1992).

Hamachi, et al., "Immobilization of myoglobin in a multi-layer film of two–dimensional polymer network," *Chem. Lett.* 2227–30 (1991).

Herbert, et al., "Neurite growth from growth dorsal root ganglia entrapped within three–dimensional fibrin gels mixed with copolymers of poly(acrylic acid) and bioactive peptides," *Dissertation* (1996).

Hoogeveen, et al., "Absorption of charged block copolymers with two adsorbing blocks," *Faraday Discuss.* 98:161–72 (1994).

Hoogeveen, et al., "Formation and stability of multilayers of polyelectrolytes," *Langmuir* 12:3675–81 (1996).

Hoogeveen, et al., "Novel water–soluble block copolymers of dimethylaminoethyl methacrylate and dihydroxypropyl methacrylate," *Macromol. Chem. Phys.* 197:2553–64 (1996).

Hubbell, et al., Endothelial cell–selective materials for tissue engineering in the vascular graft via a new receptor *Bio-Technology* 9:568–72 (1991).

Ilo, et al., "Synthesis of polyallylamine derivatives with N–carbamoylguanidine groups," *J. Polym. Sci.* 32:3189–91 (1994).

Ishihara, et al., "Selective adhesion of platelets on a polyion complex composed of phospholipid polymers containing sulfonate groups and quarternary ammonium groups," *J. Biomed. Mater. Res.* 28:1347–55 (1994).

Kataoka, et al., "Differential attachment of lymphocyte subpopulations on poly(2–hydroxyethyl methacrylate)–graft–polyamine copolymers with different degrees of quaternization," *Journal of Colloid and Interface Science* 180:242–50 (1996).

Koyo, et al., "Synthesis of novel types of segmented polyamineurea and polyamine–poly(ethylene oxide) block copolymer," *Polymer Journal* 25:141–52 (1993).

Pratten, et al., "Micelle–forming block copolymers: Pinocytosis by macrophages and interaction with model membranes", *Makromol. Chem.* 186, 725–33 (1985).

Rangarajan, et al., "Characterization of hydrogels using luminescence spectroscopy," *Biomaterials* 17:649–61 (1996).

Royappa & Rubner, "Novel Langmuir–Blodgett films of conducting polymers. 1. Polyion complexes and their multilayer heterostructures," *Langmuir* 8:3168–77 (1992).

Sittinger, et al., "Encapsulation of artificial tissues in polyelectrolyte complexes: preliminary studies," *Biomaterials* 17:1049–51 (1996).

Tam, "Synthetic peptide vaccine design:Synthesis and properties of a high–density multiple antigenic peptide system," *Proc. Natl. Sci. U.S.A.* 85:5409–13 (1988).

Tomalia & Durst, "Genealogically directed synthesis: starburst*/cascade dendrimers and hyperbranched structures" in *Supramolecular Chemistry 1: Directed Synthesis and Molecular Recognition Topics in Current Chemistry* (Weber, ed.) pp. 193–313 Springer–Verlag:Berlin (1993).

Tronin, et al., "Ellipsometry and x–ray reflectometry characterization of self–assembly process of polystyrenesulfonate and polyallylamine," *Colloid Polym. Sci.* 272:1317–21 (1994).

Wang & Huang, et al., "Synthesis of peg–dendrimeric peptide," *Chinese Chemical Letters* 7:693–94 (1996).

Willner, et al., "Development of novel biosensor enzyme electrodes:Glucose oxidase multilayer arrays immobilized onto self–assembled monolayers on electrodes," *Adv. Mater.* 5:912–25 (1993).

* cited by examiner

SEQUENCE LISTING

```
<160> NUMBER OF SEQ ID NOS: 2

<210> SEQ ID NO 1
<211> LENGTH: 5
<212> TYPE: PRT
<213> ORGANISM: artificial sequence
<220> FEATURE:
<223> OTHER INFORMATION: pentapeptide ligand

<400> SEQUENCE: 1

Tyr Ile Gly Ser Arg
1               5

<210> SEQ ID NO 2
<211> LENGTH: 4
<212> TYPE: PRT
<213> ORGANISM: artificial sequence
<220> FEATURE:
<223> OTHER INFORMATION: tetrapeptide ligand

<400> SEQUENCE: 2

Arg Glu Asp Val
1
```

MULTIFUNCTIONAL POLYMERIC TISSUE COATINGS

Priority is claimed under 35 U.S.C. §119 to PCT/US98/07590, filed Apr. 17, 1998, and to U.S. provisional application Serial No. 60/044,733 filed Apr. 21, 1997.

BACKGROUND OF THE INVENTION

This application is generally in the area of biocompatible polymeric materials which can be applied to biological and non-biological surfaces to minimize cell-cell interactions and adhesion of cells or tissue to the surfaces.

There is a need for materials, and methods of use thereof, which can be used to encapsulate cells and tissues or biologically active molecules which are biocompatible, and which do not elicit specific or non-specific immune responses. An important aspect of the use of these materials in vivo is that they must be applied within the time of a short surgical procedure or before the material to be encapsulated disperses, is damaged or dies.

It is often desirable to implant exogenous cells into a patient, for example, to produce various products the patient is incapable of preparing. An example of this is implantation of exogenous Islets of Langerhans cells to produce insulin in a diabetic patient. However, unless protected, exogenous cells are destroyed immediately following transplantation. Numerous attempts have been made to encapsulate the cells to minimize the body's efforts to destroy them.

Cells have been encapsulated using the ionic crosslinking of alginate (a polyanion) with polylysine or polyornithine (polycation) (Goosen, et al., *Biotechnology and Bioengineering*, 27:146 (1985)). This technique offers relatively mild encapsulating conditions. Microcapsules formed by the coacervation of alginate and poly(L-lysine) have been shown to be immunoprotective. However, the capsules do not remain intact long after implantation, or are quickly surrounded by fibrous tissue.

The biocompatibility of alginate-poly(L-lysine) microcapsules has been reported to be significantly enhanced by incorporating a graft copolymer of PLL and PEO on the microcapsule surface (Sawhney, et al., *Biomaterials*, 13, 863–870 (1991)). The PEO chain is highly water soluble and highly flexible. PEO chains have an extremely high mobility in water and are essentially non-ionic in structure. Immobilization of PEO on a surface has been largely carried out by the synthesis of graft copolymers having PEO side chains.

U.S. Pat. Nos. 5,573,934 and 5,626,863 to Hubbell et al. disclose hydrogel materials including a water-soluble region such as polyethylene glycol and a biodegradable region, including various biodegradable polymers such as polylactide and polyglycolide, terminated with photopolymerizable groups such as acrylates. These materials can be applied to a tissue surface and polymerized, for example, to form tissue coatings. These materials are adhered to tissue surfaces by polymerizing the photopolymerizable groups on the materials after they have been applied to the tissue surface.

U.S. Pat. No. 5,627,233 to Hubbell et al. discloses multifunctional polymeric materials for use in inhibiting adhesion and immune recognition between cells and tissues. The materials include a tissue binding component (polycation) and a tissue non-binding component (polynonion). In particular, Hubbell discloses various PEG/PLL copolymers, with molecular weights greater than 300, with structures which include AB copolymers, ABA copolymers, and brush-type copolymers. These polymers are being commercially developed for use as tissue sealants and to prevent surgical adhesions.

It is therefore an object of the present invention to provide a polymeric material that can be applied to living cells and tissues, in a very short time period, to protect the cells and tissues from cell to cell interactions, such as adhesion.

It is a further object of the present invention to provide a polymeric material which is biocompatible and resistant to degradation for a specific time period.

It is a further object of the present invention to provide compositions for inhibiting tissue adhesion and cell-cell contact within the body, as well as methods for making and using the compositions.

SUMMARY OF THE INVENTION

Compositions for encapsulating cells and for coating biological and non-biological surfaces, which minimize or prevent cell-cell contact and tissue adhesion, and methods of preparation and use thereof, are disclosed. Embodiments include polyethylene glycol/polylysine (PEG/PLL) block or comb-type copolyrners with high molecular weight PLL (greater than 1000, more preferably greater than 100,000); PEG/PLL copolymers in which the PLL is a dendrimer which is attached to one end of the PEG; and multilayer compositions including alternating layers of polycationic and polyanionic materials. In the PEGIPLL dendrimers, the molecular weight of the Pit is between 1,000 and 1,000,000, preferably greater than 100,000, more preferably, between 300,000 and 800,000, and the molecular weight of the PEG is between 500 and 2,000,000, preferably greater than 50,000. more preferably between 5,000 and 100,000. For PEG of MW 5000, the optimal ratio is between 1 PEG chain for every 3 to 10, preferably 5 to 7, lysine subunits. The optimal ratio for PEG of a molecular weight other than 5000 can be determined using routine experimentation, for example, using the procedures outlined in Example 1. In general, PEG/PLL grafts of various ratios are synthesized, for example, by varying the relative stoichiometric amounts of each component used in a suitable coupling reaction, and their relative efficacy in preventing a model binding interaction can then be determined. One method for doing this involves determine the extent of cell spreading on an anionic polystyrene surface, either uncoated or coated with the polymers.

The dendrimer is covalently grafted to one end of a PEG block. The dendrimer is a lysine dendrimer which preferably contains between 16 and 128 reactive amine groups, which correlates to a dendrimer of between generation 4 and generation 7. The molecular weight of the PEG is between 500 and 2,000,000, preferably between 5,000 and 100,000.

The multi-layer polymeric material is formed by the ionic interactions of a polycation and a polyanion. There are preferably greater than five alternating layers, more preferably more than ten alternating layers, and most preferably, greater than fifteen alternating layers of the polycationic and polyanionic materials. In a preferred embodiment, the topmost and/or bottommost layers are prepared from materials which include a polycationic tissue binding domain and a nonionic non-tissue binding domain, such as PEG/PLL copolymers.

The polymer is applied in a fluid phase to the tissues or cells to be protected, whereupon the tissue binding domains adsorb the polymeric material to the tissue. The fluid phase can be applied to isolated tissue or to tissue during surgery or by means of a catheter or other less invasive device.

The PEG/PLL copolymers can be used for inhibiting cell-cell contact and tissue adhesion. The PLL polymer adsorbs to cells or tissue, and the PEG polymer does not adsorb to tissue. When the two-domain polymeric material contacts a tissue surface, the tissue-binding domain(s) binds and immobilizes the attached non-binding domain(s), which then generally extends away from the tissue surface and sterically blocks the attachment of other tissues.

The materials can be applied to isolated tissue or to tissue during surgery or by means of a catheter or other less invasive device. The compositions are useful for blocking adhesion and immune recognition and thus may be useful in the treatment of many diseases and physiological disorders, including the prevention of postoperative adhesions, protecting injured blood vessels from thrombosis and intimal thickening relating to restenosis, and decreasing the extent of metastasis of tumor cells in tissues. The materials can be used, for example, as semipermeable membranes, as adhesives as tissue supports, as plugs, as barriers to prevent the interaction of one cell tissue with another cell or tissue, and as carriers for bioactive species. A wide variety of biological and non-biological surfaces, with different geometries, can be coated with these polymeric materials.

BRIEF DESCRIPTION OF THE FIGURES

In FIG. 1A, the substrate is tissue culture plates formed of polystyrene which has been rendered anionic by surface treatment (TCPS) and the electrolytes are polylysine (PLL) and alginate. In FIG. 1B, the substrate is TCPS coated with gelatin and the electrolytes are PLL and alginate. In FIG. 1C, the substrate is human foreskin fibroblast cells extracellular matrix (HFF ECM) and the electrolytes are PLL and alginate. In FIG. 1D, and the electrolytes are polyethylene imine (PEI) and polyacrylic acid (PAA). The squares represent spread cells, and the circles represent adhered cells.

DETAILED DESCRIPTION OF THE INVENTION

Figure 1A:
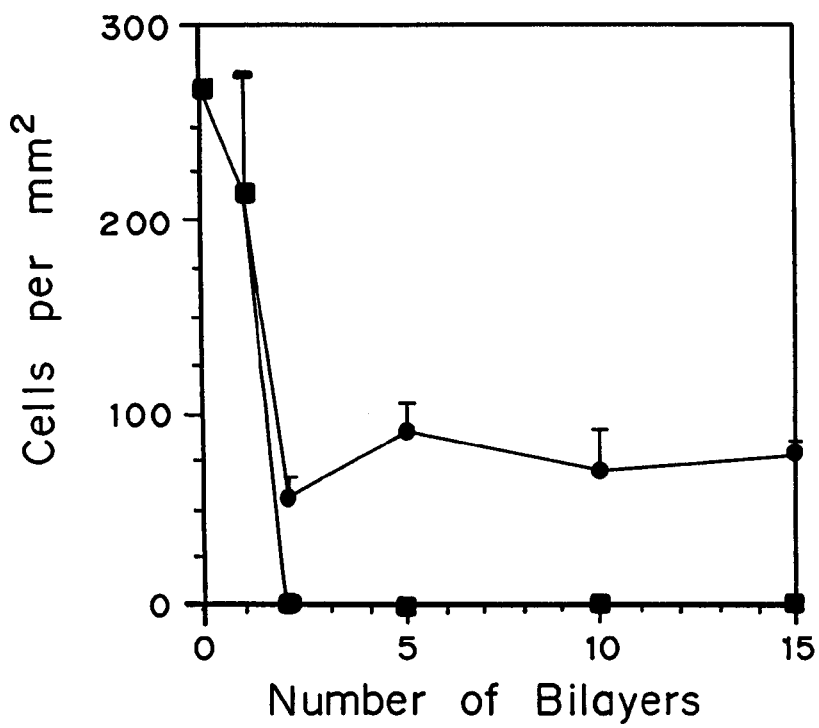
FIGS. 1A–D are graphs of the spreading of human foreskin fibroblast cells (HFF cells) (cells per $mm^2$) on various substrates coated versus the number of polyelectrolyte bilayers.

Compositions for encapsulating cells and for coating biological and non-biological surfaces, which minimize or prevent cell-cell contact and tissue adhesion, and methods of preparation and use thereof, are disclosed. The compositions are either specific PEG/PLL copolymers or multilayer materials formed of alternating layers of polyelectrolytes. The compositions can be used, for example, to plug, seal, support or coat tissue or other surfaces to alter cellular adhesion to the surface.

I. Compositions

The materials are biocompatible. Materials are considered biocompatible if the material either elicits a reduced specific humoral or cellular immune response or does not elicit a nonspecific foreign body response that prevents the material from performing the intended function, and the material is not toxic upon ingestion or implantation. The material must also not elicit a specific reaction such as thrombosis if in contact with the blood.

A. PEG/PLL Copolymers.

1. Polymer Composition

The following definitions apply to the PEG/PLL copolymers described herein. Block copolymers are defined as copolymers in which a polymeric block is linked to one or more other polymeric blocks. This is distinguished from random copolymers, in which two or more monomeric units are linked in random order to form a copolymer. Brush copolymers (as in a bottle brush) are copolymers which have a backbone of one composition and bristles of another. These copolymers are also known as comb copolymers. The terms brush and comb are used interchangeably. Dendritic polymers, also known as dendrimers or starburst polymers, are polymers which include a core molecule which is sequentially reacted with monomers with three or more reactive groups, such that at each sequential coupling step, the number of reactive groups at the ends of the polymer increases, usually exponentially. A dendron is a subunit of a dendrimer, the cone shaped structure resulting from sequential reactions starting with a core containing only reactive group. As used herein, molecular weight refers to weight average molecular weight, unless otherwise specified. As used herein, PEG is an abbreviation for polyethylene glycol, also known as polyethylene oxide or polyoxyethylene. The phrase "(meth)acrylic" refers to either acrylic or methacrylic groups.

a. PEG/PLL Brush or Comb-Type Graft Copolymers.

The PEG/PLL co-polymers can be brush copolymers (as in a bottle brush, with a backbone of one composition and bristles of another) with a backbone of polylysine (PLL) and bristles of polyethylene glycol (PEG). The molecular weight of the PLL is between 1,000 and 1,000,000, preferably greater than 100,000, more preferably, between 300,000 and 800,000. The molecular weight of the PEG is between 500 and 2,000,000, more preferably between 5,000 and 100,000.

The PEG/PLL co-polymers can be brush copolymers (as in a bottle brush, with a backbone of one composition and bristles of another) with a backbone of polylysine (Pit) and bristles of polyethylene glycol (PEG). The molecular weight of the PLL is between 1,000 and 1,000,000, preferably greater than 100,000, more preferably, between 300,000 and 800,000. The molecular weight of the PEG is between 500 and 2,000,000, preferably greater than 50,000, more preferably between 5,000 and 100,000.

Various tissue binding polycationic polymers can be substituted for PLL, and various non-tissue binding polymers can be substituted for PEG.

Suitable polycationic blocks include natural and unnatural polyamino acids having net positive charge at neutral pH, positively charged polysaccharides, and positively charged synthetic polymers. Representative polycationic blocks include monomeric units selected from the group consisting of lysine, histidine, arginine and ornithine. Representative positively charged polysaccharides include chitosan, partially deacetylated chitin, and amine-containing derivatives of neutral polysaccharides. Representative positively charged synthetic polymers include polyethyleneimine, polyamino(meth)acrylate, polyaminostyrene, polyaminoethylene, poly(aminoethyl)ethylene, polyaminoethylstyrene, and N-alkyl derivatives thereof. Suitable non-tissue binding polymers include mixed polyalkylene oxides having a solubility of at least one gram/liter in aqueous solutions, neutral water-soluble polysaccharides, polyvinyl alcohol, poly-N-vinyl pyrrolidone, non-cationic poly(meth)acrylates and combinations thereof can be substituted for PEG.

For example, PEG reacted with polyethylene imine with a molecular weight greater than 10,000 will have approximately the same physical properties as the PEG/PLL copolymers described herein. Polyhydroxyethyl methacrylate can be reacted with a suitable stoichiometric ratio of a reagent such as tresyl or tosyl chloride (an activating agent), which converts some of the hydroxy groups to leaving groups. These leaving groups can be reacted with polycationic polymers, for example, polyaminoethyl methacrylate with a molecular weight greater than 10,000, to yield a high molecular weight polymer. A suitable stoichiometric ratio is one mole activating agent per mole of polyhydroxyethyl methacrylate, and one mole activated polyhydroxyethyl methacrylate per every 3 to 9, preferably 5 to 7 moles of reactive groups on polyaminoethyl methacrylate. Suitable cationic polymers are those that, when combined with a suitable non-tissue binding polymer, have roughly the same physical properties as the PEG/PLL copolymers described herein.

b. PEG/PLL Dendrimers

The PEG/PLL dendrimers are copolymers where one or more linear PEG polymeric blocks are covalently linked to the focal point of a cationic dendrimer, for example, dendrimerically polymerized polylysine, such that the dendrimer fans out from the PEG. Preferably, the PEG is linked to the central point of the dendrimer, which is grown from the PEG as described in detail below. The particular utility of the dendritic construction is the ability to precisely control the mass of the resulting copolymer, the geometrical relationship between the polymeric blocks, and the degree of substitution. For instance, in the examples shown, there is exactly one PEG for a defined number of positive charges. In contrast, grafting preformed PEG molecules onto a polycationic backbone normally results in a random positioning of the PEG groups on the backbone.

The dendrimer preferably contains between 16 and 128 reactive amine groups, which correlates to a dendrimer of between generation 4 and generation 7. The molecular weight of the PEG is between 500 and 2,000,000, preferably between 5,000 and 100,000.

The amine groups in copolymers listed in the Examples are the primary amines of lysine residues, but other groups can be used. For example, the last "generation" of the polymer can be prepared using arginine or histidine, resulting in guanidino or imidazoyl cationic groups, respectively. Likewise, more than one PEG group can be provided, for example, by using as a starting material a small molecule with at least two carboxyl groups and at least two amino groups, for example, the dipeptide Glu-Lys.

For all embodiments, the molecular weight and number of PEG blocks per lysine block is determined such that the resulting copolymer has the properties of both the PLL and the PEG. If the proportion of PEG is too high, the bioadhesion of the polymer is reduced. If the proportion of PLL is too high, the ability of the PEG to minimize cell-cell interactions and tissue adhesion is reduced. The polymers must have sufficient PEG character to minimize cell-cell and tissue interactions. Polymers with too few PEGs per PLL are less suitable for minimizing these interactions. The polymers must also have sufficient PLL character to adequately bind to a tissue or cell surface. Polymers with insufficient PLL character fail to bind adequately to a tissue or cell surface.

Although the copolymers are described above with respect to PEG and PLL, the same activities can be obtained from variants of these polymers. Various non-tissue binding polymers can be used in place of or in addition to PEG, for example, polyalkylene oxides having a solubility of at least one gram/liter in aqueous solutions, such as some poloxamer nonionic surfactants, many neutral polysaccharides, including dextran, ficoll, and derivatized celluloses, polyvinyl alcohol, non-cationic polyacrylates, such as poly(meth) acrylic acid, and esters amide and hydroxyalkyl amides thereof, and combinations thereof. The polycationic polymer can be any biologically acceptable polycation that provides a sufficient amount and density of cationic charges to be effective at adhering to cells and tissue. A number of suitable compounds are listed below in section B(1).

The dendrimeric PLL allows the formation of a compact structure, with a high charge density. These PEG-lysine dendrons are effective in preventing cell spreading when adsorbed to a simple anionic surface if the polymer contains about 8 or more positive charges (generation 3 dendron).

The copolymer can prevent hemagglutination of human red blood cells by a lectin, if, in the presence of PEG-lysine dendron at a concentration in aqueous solution of 1% or greater, if the polymer contains about 32 or more positive charges (generation 5 dendron).

It has been assumed by others that PLL of MW higher than 40,000 could not be used to synthesize PLL-PEG graft copolymers (PLL-g-PEG), because of the toxicity of higher MW PLL. However, PLL-g-PEG is extremely well tolerated by cells in culture, in contrast to PLL. PLL-g-PEG copolymers with a PLL backbone of MW 375,000 exhibit enhanced efficacy in some in vitro models, presumably due to enhanced adsorption to biological surfaces as compared with PLL-g-PEG copolymers of lower MW. PLL-g-PEG copolymers with backbones of PLL with MW 375,000 were able to prevent fibroblast spreading onto surfaces containing pre-adsorbed serum proteins, and additionally can prevent the recognition of red blood cell surfaces by lectins. The relatively high MW PLL backbone (greater than 1,000, preferably greater than 100,000) is necessary to achieve these results.

Other non-lysine based dendrimers can also be prepared and are intended to be within the scope of the PEG/PLL dendrimers described herein. For example, the dendrimers can include polycationic groups other than amines, for example, quaternary ammonium salts. Further, synthetic, non-amino acid based cations can be included. Cationic amino acids such as ornithine can also be incorporated into the dendrimers.

2. Additional Polymeric Components

Additional domains, linking groups, and bioactive materials can be added to this basic two-domain structure. Examples of suitable domains include bioadhesive molecules, domains which convert from a binding domain to a non-binding domain in vivo, and domains which convert from a non-binding domain to a binding domain in vivo. Examples of suitable linking groups include biodegradable linkages, such as anhydride, ester, amide and carbonate linkages. Examples of suitable bioactive materials include proteins, polysaccharides, organic compounds with drug activity, and nucleic acids. The domains and/or linkages can confer adhesion to particular types of cells or molecules or degradation by enzymatic or non-enzymatic means. The domains may be a third type of polymer, for example, a biodegradable polymer such as a polyanhydride, polyhydroxy acid or polycarbonate. When serving to direct attachment, a peptide such as RGD, or even a single amino acid, which is used to target a polyamino acid for cleavage by an enzyme, can be incorporated into the polymer structure.

Photopolymerizable substituents, including acrylates, diacrylates, oligoacrylates, dimethacrylates, or oligomethacrylates, and other biologically acceptable photopolymerizable groups, can also be added to the polymeric materials. These can be used to further polymerize the polymer once it is in contact with tissue or other surfaces, which can result in improved adherence to the surface.

B. Polycationic—Polyanionic Polymer Complexes

1. Polycationic Polymers

The polycationic material can be any biocompatible water-soluble polycationic polymer, for example, any polymer having protonated heterocycles attached as pendant groups. As used herein, "water soluble" means that the entire polymer must be soluble in aqueous solutions, such as buffered saline or buffered saline with small amounts of added organic solvents as co-solvents, at a temperature between 20 and 37° C. In some embodiments, the material will not be sufficiently soluble (defined herein as soluble to the extent of at least one gram per liter) in aqueous solutions per se but can be brought into solution by grafting the polycationic polymer with water-soluble polynonionic materials such as polyethylene glycol.

Representative polycationic materials include natural and unnatural polyamino acids having net positive charge at neutral pH, positively charged polysaccharides, and positively charged synthetic polymers. Examples of suitable polycationic materials include polyamines having amine groups on either the polymer backbone or the polymer sidechains, such as poly-L-lysine and other positively charged polyamino acids of natural or synthetic amino acids or mixtures of amino acids, including poly(D-lysine), poly(ornithine), poly(arginine), and poly(histidine), and nonpeptide polyamines such as poly(aminostyrene), poly(aminoacrylate), poly (N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan. Polylysine is a preferred material. In some embodiments, the polycationic material is covalently grafted to a non tissue-binding polymer, and this material is used to form at least one of the multilayers, preferably the topmost or bottommost layer.

In general, the polymers must include at least five charges, and the molecular weight of the polycationic material must be sufficient to yield the desired degree of binding to a tissue or other surface, having a molecular weight of at least 1000 g/mole.

2. Polyanionic Polymers

The polyanionic material can be any biocompatible water-soluble polyanionic polymer, for example, any polymer having carboxylic acid groups attached as pendant groups. Suitable materials include alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. Polyphenolic materials such as tannins and lignins can be used if they are sufficiently biocompatible. Preferred materials include alginate, pectin, carboxymethyl cellulose, heparin and hyaluronic acid.

In general, the molecular weight of the polyanionic material must be sufficient to yield strong adhesion to the polycationic material. The lengths of the polycationic and polyanionic materials which would result in good blockage of adhesive interactions may be determined by routine experimentation. It should be understood that "good" is a word that must be defined by the requirements of the particular circumstance at hand, e.g., how long binding is required and how complete a repulsion is required by the particular medical application.

3. Attachment of Bioactive Species

Bioactive species can be attached to the ends of the polymers, either covalently or ionically, or by mixing the bioactive species with the polymeric material, preferably before it is applied to the cells or tissue.

A wide variety of biologically active materials can be encapsulated or incorporated, including proteins such as antibodies, receptor ligands and enzymes, peptides such as adhesion peptides, sugars, oligosaccharides, and polysaccharides, organic or inorganic drugs, nucleic acids, and cells, tissues, sub-cellular organelles or other sub-cellular components.

Bioactive species may be used to target adhesion of the polymeric material, to effect a biological activity at the polymeric material-tissue interface, or to effect an activity when the bioactive species is released during degradation of the polymeric material.

An example of a suitable ligand is the pentapeptide Tyr-Ile-Gly-Ser-Arg (YIGSR), which supports endothelial, smooth muscle cell, and fibroblast adhesion, but not platelet adhesion; or the tetrapeptide Arg-Glu-Asp-Val (REDV), which has been shown to support endothelial cell adhesion but not that of smooth muscle cells, fibroblasts, or platelets, as described in Hubbell, et al., *BioTechnology* 9:568–572 (1991). YIGSR, from laminin, binds to receptors on endothelial cells, but not on blood platelets. Thus, the conjugation of the oligopeptide YIGSR to the termini of the (A)x and adsorbing the polymeric material to a damaged vessel wall would be expected to block thrombosis on the vessel wall but not to block re-endothelialization from the surrounding undamaged vessel wall. This embodiment makes it possible to cover an injured vessel wall to prevent thrombosis but, via an adhesion ligand on the termini of one or more of the polymeric components, to permit the regrowth of endothelial cells upon the polymer. This approach also permits the re-endothelialization of the vessel wall while it is still not adhesive to platelets, thus enabling healing while avoiding platelet activation and thrombus formation.

4. Formation of Polymeric Multilayers

Polymeric multilayers can be formed by alternating application of polyanions and polycations to surfaces to form coacervated coatings. Multilayers of coacervated polyions can be formed on macroscopic tissue surfaces, including mammalian tissue surfaces, and thereby provide various benefits to the coated surfaces. These include the prevention of adherence of tissue to tissue, or of cells to tissue, or provision of selective adherence, as described below. Use of macroscopic tissues as the substrate avoids the problems associated with the coating of individual cells or groups of cells as has been done by others, since the tissue is generally vascularized and is therefore provided with nutrients, oxygen and waste product removal. The layers can be used to encapsulate, plug, seal, or support a macroscopic surface. The application of a multilayer coating can be used to minimize or prevent tissue adhesion, minimize or prevent postoperative adhesions, prevent thrombosis, prevent implantation of cancerous cells, coat tissue to encourage healing or prevent infection, or enhance the local delivery of bioactive agents. Preferably, at least four layers, and, more preferably, at least six layers are used to form the coatings.

5. Assembly of Complexes with Anion-Cation Coupling

Microscopic structures can be produced by successive incubation of a surface with solutions of polyionic compounds. In this embodiment, a solution including a polycation is applied to a surface, the excess solution washed off of the surface, and a solution including a polyanion is then applied to the surface. This process is repeated until the desired thickness is obtained. This process is referred to herein as "multilayer techniques". If only a monolayer of each polyelectrolyte adsorbs with each incubation, then electrostatically crosslinked hydrogel-type materials can be built on a surface a few microns at a time. In another embodiment, the surface is not thoroughly rinsed between the application of the polycation and the polyanion. This leads to the formation of thicker, hydrogel-like structures. The multilayers tend to be relatively bioinert without further treatment, and are effective at preventing cell spreading on an extracellular matrix surface. The multilayers can be used, for example, to form protective barriers during surgery. An apparatus equipped with a spray nozzle can be used, for example, to spray a layer at a time of a polycation followed by a layer of a polyanion. Alternatively, both polyelectrolytes can be sprayed simultaneously to create relatively thicker layers.

6. Thickness and Conformation of Polymer Layer

Membrane thickness affects a variety of parameters, including perm-selectivity, rigidity, and size of the membrane. Thickness can be varied by selection of the reaction components and/or the reaction conditions. When alternating layers of polycationic and polyanionic materials are used, the layer thickness can be controlled by adjusting the number of layers and also the degree of rinsing between layers. In spraying layers, control of drop size and density can provide coatings of the desired thickness without necessarily requiring rinsing between layers. Additionally, the excess (unbound) material can be removed via other means, for example, by an air jet.

If the residual polyelectrolyte from the previous layer is substantially removed before adding the subsequent layer, the thickness per layer decreases. Accordingly, in a preferred embodiment, the surface is first coated with a polycation, the excess polycation is removed by rinsing the surface, the polyanion is added, the excess is removed, and the process is repeated as necessary.

By increasing the number of cycles, for example, to 50 or higher, the polymer systems can be used to generate thick, non-adhesive films.

II. Synthesis of Polymeric Materials

A. Synthesis of PEG/PLL Copolymers

PEG may be bonded to the famines of lysine residues of poly(L-lysine) as follows. Poly(L-lysine) (PLL) can be reacted with a PEG with one end protected (i.e., a protected monomethoxy PEG), the terminal hydroxyl of which has been previously activated with carbonyldiimidazole (CDI). The PLL and the activated PEG can be mixed in an aqueous solution buffered at pH 9 and allowed to react for 48 hours at room temperature. The number of PEG chains grafted per PLL chain may be controlled by adjusting the ratio of moles of activated PEG added per mole of added PLL. The reaction may not proceed to completion, i.e., the mole ratio of PEG to PLL in the reaction mixture may not be identical to that in the PEG-b-PLL product, but higher ratios of PEG to PLL will produce higher amounts of PEG in the PEG-b-PLL product.

The cationic domains tend to be highly reactive, and efforts must be made to control the extent of addition of PEG to PLL. Executing the reaction in the absence of water reduces deactivation of PEG and allows better stoichiometric control. For example, unprotected poly-L-lysine can be dissolved in water, then added to dimethylformamide (DMF) to make a solution that is 5% aqueous. The poly-L-lysine can then be reacted with CDI mono-activated PEG in stoichiometric amounts, followed by evaporation of solvent under vacuum yielding a PEG/PLL copolymer. Alternatively, unprotected poly-L-lysine can be dissolved in water and precipitated by adding NaOH. The precipitated polymer can then be added to anhydrous DMF and then reacted with CDI mono-activated PEG in stoichiometric amounts, yielding an (A)x-b-(B)y copolymer. When the reaction is performed in the absence of water, side reactions involving the activated group can be reduced (i.e., deactivation is reduced), and at long reaction times the ratio of mole PLL to PEG in the polymer product more closely resembles than in the reactant mixture.

Solution polymerization of PLL may be carried out using monomers containing different epsilon protecting groups, which allows strict control over the degree of substitution of PEG onto PLL. N-carboxy anhydrides of various amino acids may be synthesized and polymerized into copolymers, as in the following example. N,N'-dicarbobenzoxy-L-lysine (Z,Z-lysine) can be reacted with phosphorus pentachloride to yield α,N-carbobenzoxy-α,N-carboxy-L-lysine anhydride. α,N-carbobenzoxy-α,N-tert-butyloxycarbonyl-L-lysine (Z,boc-lysine) can be reacted with sodium methoxide to yield the sodium salt of Z,boc-lysine. The sodium salt of Z,boc-lysine can be reacted with phosphorus pentachloride to yield α,N-tert-butyloxycarbonyl-α,N-carboxy-L-lysine anhydride. Z,Z-lysine anhydride can be added to Z,boc-lysine anhydride, and the two monomers can be polymerized by the addition of sodium methoxide as an initiator. A copolymer results, poly(α boc-lysine)-co-(α Z-lysine). The boc groups can be removed by addition of the polymer to trifluoroacetic acid for fifteen minutes.

The salt form can be converted to the free base by reaction with a reactant such as pyridine. The free amines on the polymer can then be reacted with CDI PEG in DMF. The Z groups can then be deprotected by adding the polymer to HBr in acetic acid for fifteen minutes, yielding an (PEG)x-b-(PLL)y copolymer, where the ratio of PEG to PLL in the final product can be controlled by the initial ratio of boc protected lysines.

It may be desirable to produce versions of the polymer which are not of a brush structure. This may be facilitated by not deprotecting the epsilon amines of PLL, so that the only reactive groups are the amine and carboxyl termini. For example, reaction of CDI mon-activated PEG with poly α,N-carbobenzoxy-L-lysine in DMF yields an (A)x-(B)y copolymer. Activation of the carboxyl terminus of the (A)x-(B)y copolymer with TSU followed by reaction with mono-amino PEG in DMF yields an (A)x-(B)y-(A)z copolymer.

In some embodiments, it may be desirable to incorporate biodegradable polymers such as polylactides, polyanhydrides, or polycarbonates. For example, monomethoxy PEG reacts with d,l-lactide (1:3 molar ratio) in xylene in the presence of stannous octate under reflux for sixteen hours to yield a PEG with an end group which degrades over time in water. The hydroxyl at the terminus of the trilactide end group can be activated with CDI, which can then further reacted with PLL by methods presented above to yield an (A)xC-b-(B)y, an (A)xC-(B)y or an (A)xC-(B)y-C(A)z copolymer. Similar nucleophilic displacement chemistry can be used to couple other biodegradable polymers to the PEG backbone.

In some embodiments, it may be desirable to incorporate a polymeric material with a non-binding backbone which is converted to a binding backbone through degradable linkages. For example, the terminal amine on polyglutamic acid can be reacted with CDI PEG to produce an (A)x(D)y-b-(B)y copolymer. The copolymer can be dissolved in water at pH 2 and lyophilized to convert the carboxylic acid salt to the free acid. The polymer can be dissolved in DMF, and the glutamic acid residues activated with TSU. The activated polymer can then be reacted with boc protected aminoethanol in DMF overnight at room temperature and then deprotected and desalted. The resulting product is initially polycationic and binding, but hydrolyses to a non-binding polyanion.

In other embodiments it may be desirable to incorporate a material which converts over time from a material which is repulsive to cells to one which is non-repulsive to cells. For example, a polypeptide may be reacted with an (unprotected) hydroxy acid using peptide synthesis techniques to yield a nonionic polymer. Over time, as the amide linkage degrades, the nonion converts from repulsive to not repulsive.

B. Optimization of the Polymeric Material for Individual Applications

The biological performance of these materials can be optimized by altering the structure of the polymers, the ratio of the number of tissue-binding polymers to non-binding polymers, and the ratio of the mass of the tissue-binding polymers to non-binding polymers.

In some cases, polymeric materials exhibiting more than one manner of degradation may be required to achieve different results. For example, degradation by nonenzymatic hydrolysis will depend primarily upon the accessibility of the polymeric material to water and the local pH. Given that pH and water concentration are similar throughout many parts of the body, such a mode of degradation would yield a loss in repulsiveness of the polymer that depends mostly upon time. As another example, if the degradable region is sensitive to an enzyme, the activity of which is not highly regulated but rather was present in the body fluids at a more or less constant level, the rate of loss of repulsiveness depends primarily upon time. As another example, if the degradable region is sensitive to an enzyme, the activity of which is more highly regulated, the rate of loss of repulsiveness will depend more upon the expression of that particular enzyme activity. For example, many types of cells express the proteases plasmin or collagenase during migration. Sensitivity to plasmin by the polymer allows the polymer to be degraded by cells migrating onto the surface, so that they can attach to recolonize the surface. This is particularly useful in prevention or treatment of restenosis.

The biological performance of these polymeric materials depends upon their structure. Specific features of biological performance include binding to the tissue, repulsion of opposing tissues, duration of binding to the tissue, duration of repulsion of opposing tissues, and the mode of loss of binding or repulsion. Specific features of polymeric material structure include the type (chemical composition) of tissue-binding domain, type of non-binding domain, the ratio of the mass of binding to non-binding domains, the number of binding to non-binding domains, the inclusion of sites that are particularly susceptible to nonenzymatic hydrolysis, the inclusion of sites that are particularly susceptible to enzymatic hydrolysis, and the inclusions of sites with particular biological affinity.

C. Method for Forming Polymeric Materials

Polymeric objects can be formed into a desired shape by standard techniques known to those skilled in the art, for example, using casting, molding, or solid free form techniques such as three dimensional printing techniques. For example, a mask can be used to cover a specific area in a layer in which a polyelectrolyte is not to be added. The shape of the object can be controlled as subsequent layers are added.

The materials may also be shaped in relative to an internal or external supporting structure. Internal supporting structures include screening networks of stable or degradable polymers or nontoxic metals. External structures include, for example, casting the gel within a cylinder so that the internal surface of the cylinder is lined with the gel containing the biological materials.

III. Methods of Use

The materials have a variety of applications. These include local application, either at the time of surgery or via injection into tissue, to prevent adhesion of tissues; to deliver bioactive compounds where release is effected more efficiently or at a more desirable rate or where tissue encapsulation could detrimentally affect or delay release; to prevent thrombus formation at blood vessel surfaces, for example, following angioplasty; to alter cellular attachment, especially to prevent cellular attachment, and therefore decrease metastasis of tumor cells; and to coat prosthetic implants such as heart valves and vascular grafts derived from processed tissues.

As defined herein, "tissue" includes tissues removed from the body and tissues present in the body, but specifically excludes cells and cell aggregates, because these may be adversely affected by coating them with the polymeric materials. This term can also be applied to treated tissue, such as tissue heart valves, blood vessels and membranes, where the tissue is no longer living and has been chemically fixed, or a cryopreserved blood vessel or other tissue.

The polymeric materials can be applied directly by localized or topical application, or can be delivered systemically to deliver drugs. Topical or localized application can be achieved generally by spraying or injecting a very thin layer (usually on the order of monolayers of polymeric material) onto the surface to be coated. Methods for applying the polymeric materials in this manner are known to those skilled in the art.

A. Coating of Non-Biological Surfaces

The polymeric materials can also be applied to a non-biological, preferably anionic, surface intended to be placed in contact with a biological environment. Such surfaces include, for example, catheters, prosthetics, implants, vascular grafts, contact lenses, intraocular lenses, ultrafiltration membranes, and containers for biological materials. Additionally, cell culture dishes, or portions thereof, can be treated to minimize adhesion of cells to the dish. Cell culture dishes treated in this manner only allow cell spreading in those areas which are not treated, when the cells are anchorage dependent cells (cells which must be anchored to a solid support in order to spread).

The polymeric materials can be applied to the treatment of macrocapsular surfaces, such as those used for ultrafiltration, hemodialysis and non-microencapsulated immunoisolation of animal tissue. The surface may be in the form of a hollow fiber, a spiral module, a flat sheet or other configuration.

B. Coating of Metal and Ceramic Surfaces

Metal surfaces in contact with biological fluids can be coated with the polymeric materials. Absent such a coating, these surfaces can be quickly fouled by adsorption of a protein layer when in contact with biological fluids. Deposition of biological matter is minimized by coating the surfaces with the polymeric materials.

Examples of protein-repelling water soluble polymers include, but are not limited to, polyethylene glycol, polyethylene oxide, poly-N-vinyl pyrrolidone, polyhydroxyethyl methacrylate, and polyacrylic acid. The polycationic polymers include, but are not limited to, polylysine, polyarginine, and polyethylenimine.

The metals which are passivated are those that present a net anionic metal or metal oxide surface in water at physiological pH, and are used to form conduits for the flow of biological fluids, or those used to form devices in contact with biological fluids, including those devices. that are implanted into humans or animals. The metals include stainless steel and titanium, or surfaces with metal oxides such as iron oxide, titanium oxide and silicon oxide. The metals are treated with the polymer as a part of conduit or device manufacture, or are treated in situ, following assembly of the conduit or device, or as part of the normal operation of the device.

The treatment may be. applied by adsorption of the polymeric materials from a liquid solution, or by spraying. Removal of the polymer from the metal via a change in pH, or other means, may also be used as a cleaning step as a part of the normal operation of a device using this technology, as well as the reapplication of a polymer layer to the metal, resulting in a resumption of the protein-repelling properties at the treated metal surface.

The compositions and methods described herein will be more fully understood with reference to the following non-limiting examples.

EXAMPLE 1

Effect of Materials on Cell Spreading

A variety of methods can be used to optimize the desired properties. For example, when a PEG-b-PLL brush copolymer is used to protect an injured tissue surface from the adhesion of cells approaching from the fluid phase in contact with that tissue surface, the polymeric material can be optimized by conducting studies using a tissue culture model.

Fibroblasts can be seeded on a multiwell dish treated with proteins adsorbed from cell culture medium containing 10% serum. Some of the wells can be coated with the copolymers, and others can be left uncoated. Then, the surface can be seeded with fibroblasts in culture medium containing 10% serum and the adhesion and spreading can be monitored.

A measurement of the fraction of cells adhering (Fa) and fraction of cells spreading (Fs) may be made based on morphological criteria using light microscopy. Such measurements conducted 4 hours following seeding can provide useful measures of adhesion and repulsion.

The effect of cell spreading is localized to a surface. For example, when PEG/PLL is spread on a portion of a surface, only that portion of the surface resists cell adhesion. A PEG/PLL solution was spread on approximately one half of a polystyrene cell culture well. After seeding the well with fibroblast cells, cells spread on the untreated area of the well, but did not spread onto the treated half of the well. A sharp transition was observed between the untreated and treated regions.

When human foreskin fibroblast cells (HFF cells) were added to a tissue culture well coated with PEG/PLL, they did not spread. However, when the cells were transferred to an untreated well, cell spreading proceeded normally on the untreated surface.

Red blood cells can be aggregated with wheat germ agglutinin. The ability of various types of PEG/PLL polymers to minimize agglutination was evaluated. PEG/PLL copolymers with a 5 Kd PEG chain and a 375 Kd PLL chain, with graft ratios of 14, 10.5, 7.5, 7, 5.6, 3.5, 1.75 and 1.25 were prepared and evaluated. The PEG/PLL polymers with a graft ratio of 14 agglutinates RBC (even without the addition of wheat germ agglutinin), 10.5 agglutinates some of the red blood cells, and protects some of the red blood cells from wheat germ-agglutinin induced hemagglutination, 7.5 forms a complex, 7 hinders agglutination, 5.6 hinders agglutination, 3.5 slightly hinders agglutination, and 1.75 and 1.25 have no effect on agglutination. Accordingly, a useful range of graft ratios for these polymers for minimizing agglutination of RBC is between 3.5 and 10.5.

In contrast, PEG/PLL with a 5K PEG chain and a 20 KD PLL chain had either no effect on agglutination (graft ratios of between 1.75 and 7) or caused agglutination (graft ratios of 10.5 and 14). The results are summarized in Table 1.

TABLE 1

Effect of PEG/PLL on Agglutination of Red Blood Cells

| Polymer | Highest conc. of WGA with pellet formation | Highest conc. of WGA without large aggregates | Highest conc. of WGA without small aggregates | Comments |
| --- | --- | --- | --- | --- |
| PBS | 1.54 | 0.514 | 0.514 | No effect |
| mPEG 5K | 1.54 | 0.514 | 0.514 | No effect |
| PLL 20K | Agglut | Agglut | Agglut | Agglut RBC |
| PLL 418K | Agglut | Agglut | Agglut | Agglut RBC |
| Plu F-68 | 1.54 | 0.514 | 0.514 | No effect |
| 5/20 - 1.75 | 1.54 | 0.514 | 0.514 | No effect |
| 5/20 - 3.5 | 1.54 | 0.514 | 0.514 | No effect |
| 5/20 - 7 | 1.54 | 0.514 | 0.514 | No effect |
| 5/20 - 10.5 | 0.514 | 0.171 | Agglut | Agglut RBC |
| 5/20 - 14 | Agglut | Agglut | Agglut | Agglut RBC |
| 5/375 - 1.25 | 1.54 | 0.514 | 0.514 | No effect |
| 5/375 - 1.75 | 1.54 | 0.514 | 0.514 | No effect |
| 5/375 - 3.5 | 1.54 | 0.514 | 0.514 | No effect |
| 5/375 - 5.6 | 125 | 125 | 125 | Hinders agglut. by WGA, slightly |
| 5/375 - 7 | 125 | 125 | 13.9 | Hinders agglut. |
| 5/375 - 7.5 | 125 | 125 | Agglut | Complex |
| 5/375 - 10 | 125 | 125 | 125 | Hinders agglut. |
| 5/375 - 10.5 | 125 | 1.54 | 1.54 | Complex |
| 5/375 - 14 | Agglut | Agglut | Agglut. | Agglut RBC |

In Table 1, PBS indicates phosphate buffered saline. mPEG 5K indicates monomethoxy PEG with a molecular weight of 5K. PLL 20K indicates a polylysine with a molecular weight of 20K, whereas PLL 418K specifies that the molecular weight of the PLL is 418 K. Plu F-68 is a specific pluronic nonionic surfactant. 5/20 indicates that the polymer includes a PEG with a molecular weight of 5K, and PLL with a molecular weight of 20K. 5/375 indicates that the polymer includes a PEG with a molecular weight of 5K, and PLL with a molecular weight of 375K. The numbers following 5/20 or 5/375 specify the ratio of grafting of PEG to PLL.

Figure 3:
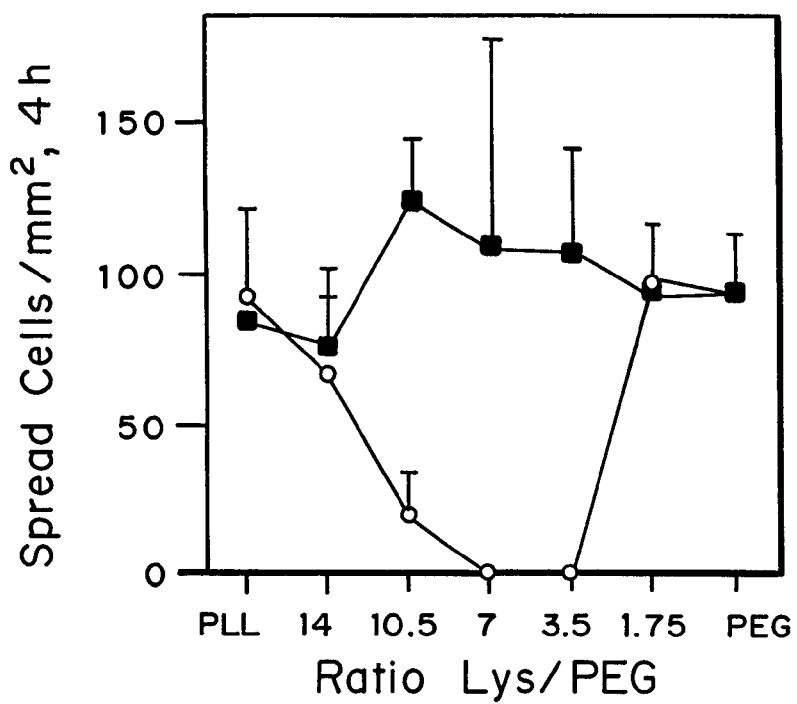
FIG. 3 is a graph of the number of spread cells/$mm^2$ after a four hour incubation versus the ratio of lysine to PEG in various graft copolymers. Squares represent copolymers of mPEG with a molecular weight of 5000 and PLL with a molecular weight of 20,000. Circles represent copolymers of MPEG with a molecular weight of 5000 and PLL with a molecular weight of 375,000.

An adsorbed serum protein substrate was incubated with PEG/PLL 5/20 and PEG/PLL 5/375. The polymers with relatively low molecular weight PLL did not lead to any change in the response of the cells to the surface. However, the series of copolymers with the higher molecular weight PLL led to a significant reduction in cell spreading on the adsorbed serum protein substrate as PEG molecules were added to the PLL backbone. Cell spreading was eliminated when the graft ratio was 7 or 3.5 and was significantly lower relative to the low molecular weight PLL when the graft ratio was 10.5. The results are shown in FIG. 3.

The data show that PLL-g-PEG polymers with a relatively low molecular weight PLL backbone allow cell spreading and those with a relatively high molecular weight PLL backbone prevent cell spreading.

EXAMPLE 2

Evaluation of PEG/PLL Dendrimers

Various model surfaces were treated with the PEG/PLL, where the PLL is in the form of dendrimers, then washed with PBS. Fibroblasts were then seeded in serum containing media, and the number of spread cells per square millimeter was counted at four hours. The results are shown in Tables 2 (a–c). The results show that as the number of amine groups is increased to 4 or more, the number of spread cells is significantly decreased.

TABLE 2

Cell Spreading on TCPS Coated with PEG/PLL dendrimers

| Dendron Generation (# of Amines) | PEG 20K | PEO 100K | PEG 5K |
|---|---|---|---|
| —OH (0) | 144 ± 13 | 83 ± 33 | 150 ± 18 |
| Y (1) | 125 ± 22 | 147 ± 21 | 118 ± 37 |
| 1 (2) | 137 ± 33 | 92 ± 39 | 132 +/− 8 |
| 2 (4) | 0 ± 0 | 33 ± 7 | — |
| 3 (8) | 0 ± 0 | 0 ± 0 | 1 ± 1 |
| 4 (16) | 0 ± 0 | 3 ± 3 | — |
| 5 (32) | 0 ± 0 | — | — |

In Table 2, —OH indicates that the polymer is PEG, with 20K, 100K, and 5K representing the molecular weight of the polymers. Y indicates a zero generation dendrimer, in which one amino group is present.

The results demonstrate that, at least with respect to TCPS surfaces, dendrimers with between 4 and 32 amine groups significantly reduced cell spreading. In all cases, spreading was reduced as the generation of the PLL dendrimer increased.

The polymers were used to assess the immobilization of PEG to the biological surfaces through adsorption of the polycationic block. The PEG dendrons were able to prevent cell spreading on a simple anionic surface, indicating that PEG was present on the surface, however, the copolymers had no effect on cell spreading on proteinaceous surfaces. Treatment of red blood cells with PEG 20K with a five generation lysine dendron (32 amines) was able to hinder hemagglutination by a lectin, however, the polymer itself was found to agglutinate red blood cells in the absence of mixing.

EXAMPLE 3

Cell Spreading on Polyelectrolyte Multilayers
HFF Cells On TCPS

In order to establish a baseline for cell spreading on polyelectrolyte multilayers, multilayers were formed onto tissue culture polystyrene (TCPS) using 0.1% PLL (MW 50,000) and 0.15% alginate, with 4 PBS washes following each adsorption step, out to 15 bilayers. On this surface, the number of well spread cells dropped to zero after the second layer was added (see FIG. 1A). However, quite a few poorly spread cells were observed on the substrates with 2 to 15 layers, with their number remaining somewhat constant out to 15 layers.

HFF Cells on Gelatin

Gelatin is produced by denaturing collagen, and substrates for tissue culture are often coated with gelatin to enhance cell attachment to a substrate. As a denatured protein, a mixture of hydrophobic and hydrophilic residues are exposed, and a very heterogeneous surface should be generated upon adsorption to a surface.

Figure 1B:
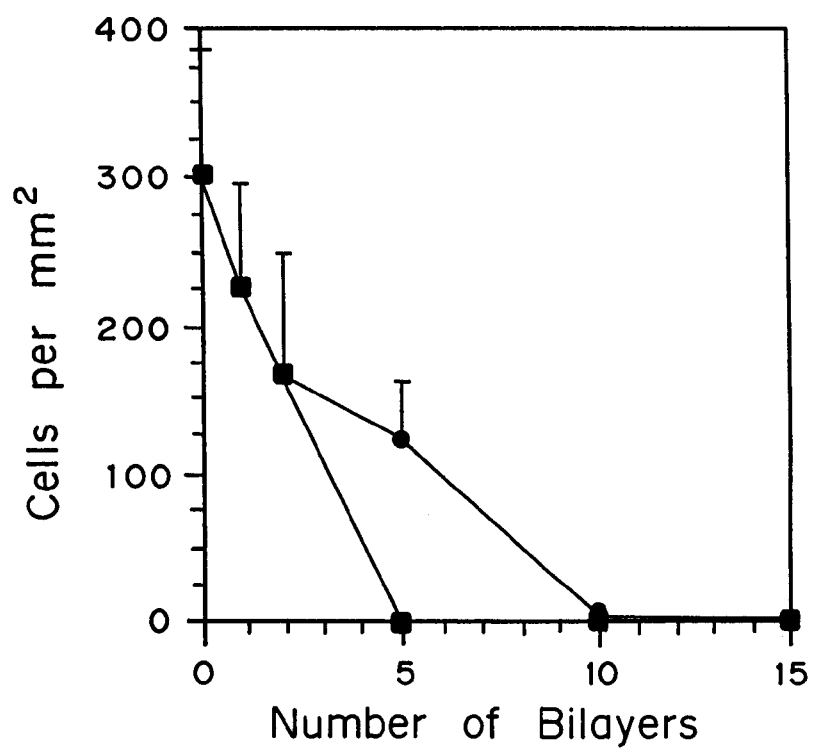

Using 0.1% PLL and 0.15% alginate, multilayer structures were formed on the gelatin coated tissue culture polystyrene substrates, with 4 deionized water washes between adsorption steps. HFF adhesion decreased on substrates with more layers, and was inhibited after formation of ten layers on the substrate (see FIG. 1B).

Figure 1C:
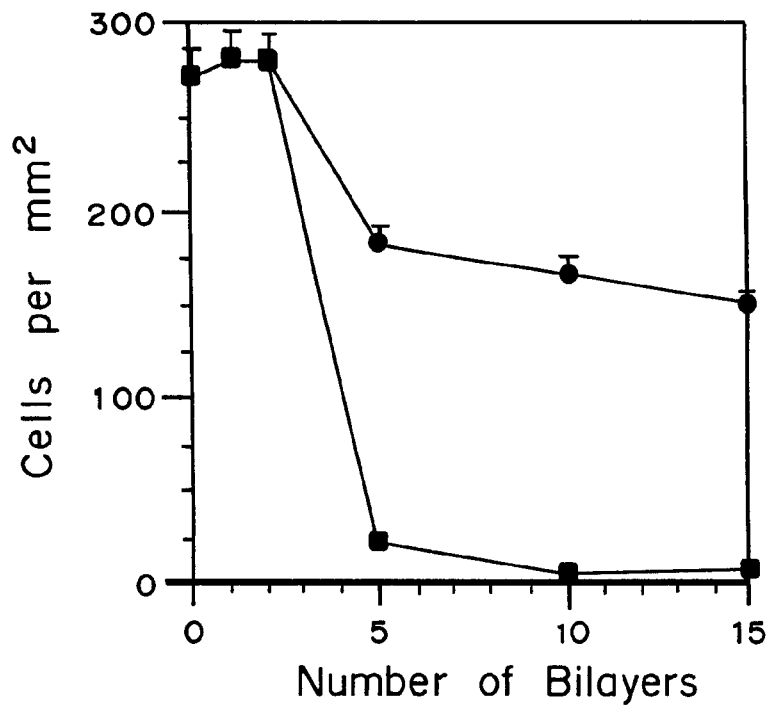
Figure 1D:
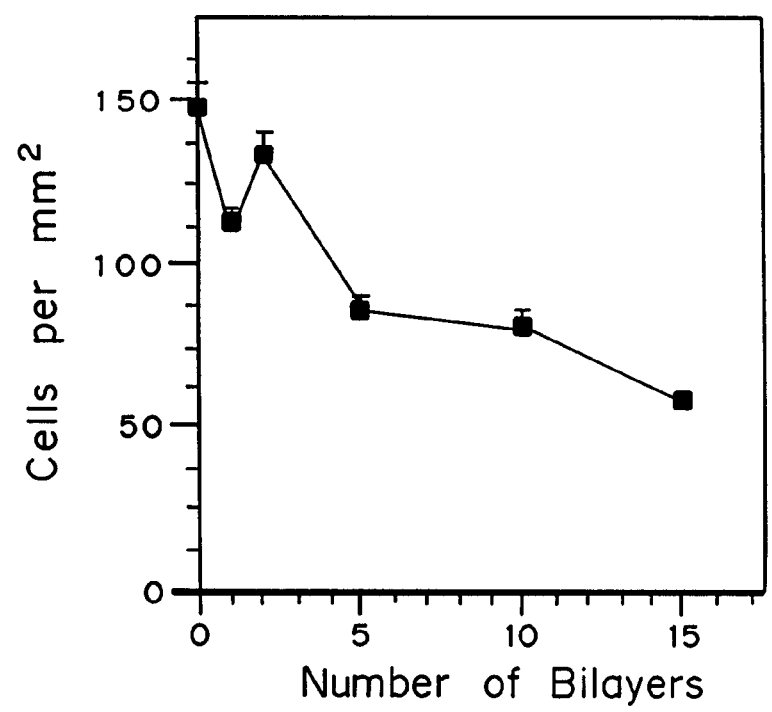

When a polyethylene imine and polyacrylic acid (PEI and PAA) (MW 50,000 for both polymers) were used in place of PLL and alginate, the number of spread cells decreased as the number of layers increased. However, the extent of lowering of cell spreading was less than that observed when PLL and alginate were used. The results are shown in FIG. 1D.

HFF Cells on HFF ECM

An extracellular matrix of fibroblasts on a surface is a good model for the surface of a damaged tissue. Fibroblasts deposit fibronectin and collagen, and many other proteins, while growing on a surface, making very cell adhesive surfaces, after the cells are removed with 0.1 N ammonium hydroxide. The presence of fibrillar collagen on the surface would greatly increase the surface roughness of the adsorbed layer, since the network of fibrils are large enough to be seen at 100x by phase contrast microscopy.

A surface was coated with human foreskin fibroblast extracellular matrix (HFF ECM). A coating was prepared by sequentially adding alternating layers of PLL and alginate, using 0.1% PLL and 0.15% alginate solutions, and washing the surface with 4 deionized water washes between adsorption steps. The spreading of HFF cells was greatly inhibited after 5 layers were applied to the surface, however, poorly spread cells were found even after 15 layers were applied. These results are similar to the results obtained with TCPS (see FIG. 1C).

Toxicity

The inhibition of cell spreading at hydrogel surfaces can be explained in terms of limited interaction of proteins with the hydrogel surface. Ideally, no other metabolic activities of the cells should be affected by the surface, and thus the cells in contact with the surface should remain viable and competent for cell spreading for up to 24 h. Polycations are known to be toxic to cells at low concentrations, and thus the effects could be a result of cellular toxicity. Therefore, viability and cell spreading were assessed for HFF cells on the TCPS substrate with 15 PLL/alginate bilayers after one hour. By adding fluorescein diacetate to the cell culture media, metabolically active cells become labeled with fluorescein by the function of esterases in the cell. The fluorescently labeled cells were counted, and it was found that 96.3% were fluorescent, indicating viability and metabolic activity after 1 hr on the multilayer surface. At this time point, cell spreading had commenced on the untreated surfaces and on surfaces with only a few bilayers, but no cells were spread on the surface with 15 bilayers.

After one hour in a TCPS well with 15 PLL/alginate bilayers, the cells in the well were moved to a new well which was untreated TCPS. The cells were moved by pipeting the media from the first well into the second well, without the addition of new media. Normal cell spreading was observed, and only well spread cells were found at 24 hours.

Additionally, a multilayer assembly formed using 1% PLL and 1.5% alginate, with 15 min. incubation times and with only one PBS wash, was formed in a tilted tissue culture well, such that only half of the well was treated. Two bilayers were formed, and cells seeded onto the well. Cells spread normally on the untreated side, and spread and migrated right up to edge of the multilayer. Cells on the side with the multilayer did not spread. The multilayers formed using these conditions are very thick, and thus toxicity due to the leaching of polymer would be more prominent in this system. The spreading of cells on the untreated side indicated that cell spreading is not inhibited in the presence of polyelectrolyte multilayers by the release of a soluble, toxic factor.

The presence of phenol red in tissue culture media allows the pH to be monitored during an experiment. No change was detected in the color of the tissue culture medium as compared to control substrates.

EXAMPLE 4

Coating of $Si/SiO_2$ Wafers with Polyelectrolytes

Figure 2:
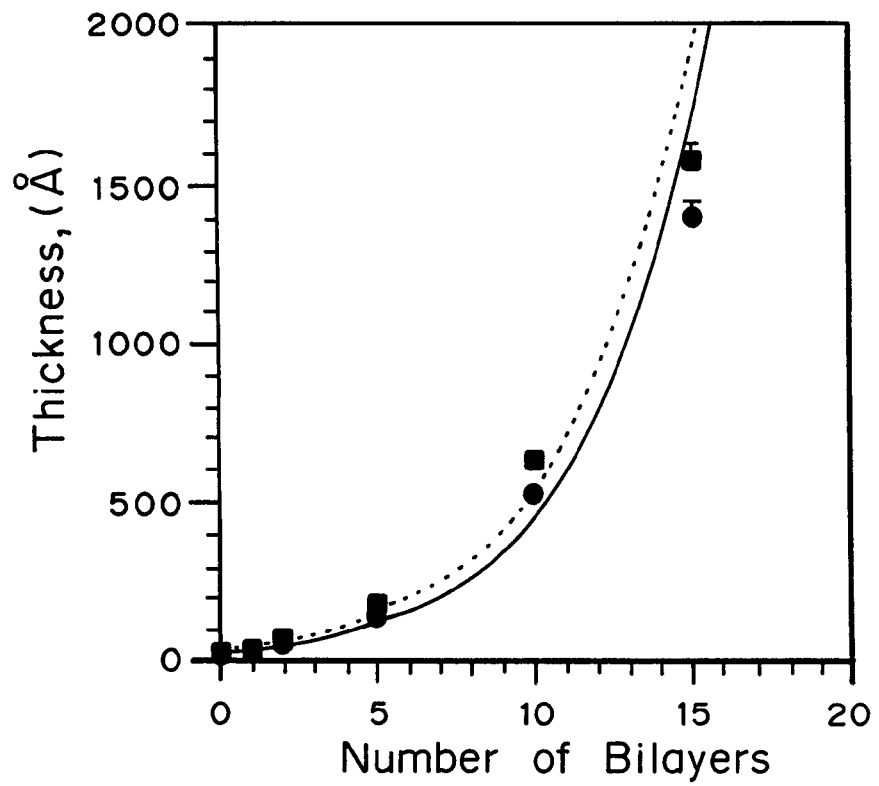
FIG. 2 is a graph of the thickness (Angstroms) of (PLL/alginate) polyelectrolyte bilayers versus the number of bilayers coated on an $Si/SiO_2$ substrate (circles) and $Si/SiO_2$ wafers coated with gelatin (squares).

Solutions containing 0.1% PLL (MW?) and 0.15% alginate, both in PBS at pH 7 were used in multilayer techniques to produce self-assembled structures on $Si/SiO_2$ wafers and $Si/SiO_2$ wafers with adsorbed gelatin. As the number of bilayers increased, so did the thickness of the layer. The thickness of the bilayers (as measured by ellipsometry) as a result of the number of bilayers is shown in FIG. 2. The ellipsometric data with the PLL and alginate system suggests that the thickness of the polymeric layers does not increase linearly.

As further evidence for formation of multilayer structures on a gelatin coated substrate, dynamic contact angles were measured as multilayers were formed on a clean glass surface coated with gelatin, as a method for detecting changes in surface chemistry. The advancing and receding contact angles for the clean glass surface were 13.4 and 11 degrees, respectively. After adsorption of gelatin, the advancing and receding contact angles were 46.4±7.0 degrees and 17.3±4 degrees, respectively. Using 0.1% PLL, and 0.15% alginate in PBS at pH 7, with four deionized water washes following the adsorption of each polyelectrolyte layer, the receding contact angle gradually decreased to under 10 degrees, but the advancing contact angle changed from about 60 degrees following deposition of a polylysine layer to about 40 degrees following deposition of an alginate layer. In the dry state, polylysine would be expected to be somewhat hydrophobic, since polylysine's hydrophilicity comes mainly from its charged amines, which would be neutral or exist as a salt in the dry state. Alginate, having numerous hydroxyl groups, would be expected to be more hydrophilic in the dry state. This data indicated that the surface of a gelatin coated substrate was being changed with each polyelectrolyte adsorption step. After addition of four bilayers of polymer, the samples became highly wettable, such that water would not readily retract from the surface following removal from water. One sample was built up to 15 bilayers. At this point, for the polylysine layer, the contact angles were 80 degrees and 7.6 degrees, advancing and receding, respectively, and for the alginate layer, the contact angles were 64.2 and 6.98 degrees.

The data indicated pairing in the progression of advancing contact angle of each gelatin substrate, and thus the change in advancing contact angle from one step to the next for each substrate was analyzed. Statistical significance was judged for each adsorption step in comparison with the previous adsorption step using ANOVA techniques. After adding the third alginate layer, the change in contact angle from one layer to the next was significant at a confidence level greater than 99.9%.

In order to correlate the cell spreading behavior with multilayer thickness, PEI and PAA multilayers were built onto $Si/SiO_2$ substrates, and thicknesses were measured by ellipsometry. Very little change in thickness was observed between 1 and 10 layers, however, a thickness of 120 Angstroms was observed at 15 layers, with a thickness per layer of 6.7 Angstroms. The thickness at 15 layers with the PEI/PAA system was similar to that observed with 5 layers in the PLL/alginate system. In both cases, the number of well spread cells was decreased to about a third of the spreading found on gelatin substrate alone. Accordingly, there is a correlation between spreading on the surface and the thickness of the polyelectrolyte coating.

Surface films prepared using the PEG/PLL copolymers and the alternating layers of polycations and polyanions are highly effective at coating and preventing cell spreading on even the most adhesive of surfaces, such as collagen Type 1, gelatin, fibroblast extracellular matrix, and fibronectin. The choice of polyelectrolytes is important—polylysine/alginate exhibits exponential growth thickness, and is effective in these models when the film thickness are greater than about 100 nm. In contrast, when the layers were prepared from polyethylene imine/polyacrylic acid, the thickness of the layer grew linearly rather than exponentially, resulting in thinner films per cycle of polycation/polyanion addition. The thickness of the layer correlated to the degree of minimization of cell spreading, so more layers are necessary to achieve the same results seen with the PLL/alginate layers.

EXAMPLE 5

Thickness of Multilayer Films is Affected by Processing Conditions

PLL and alginate multilayers tend to grow in an exponential rather than linear fashion. Other polymer layers tend to grow in a more linear fashion. A series of studies were conducted to explain the behavior of the PLL/alginate system, and to determine if the phenomenon could be generalized to other polymers.

In the formation of PLL and alginate microcapsules, wall thicknesses on the order of microns can be generated with only three polymer layers. In this case, the alginate is first gelled into a microsphere using $Ca^{++}$, and the microspheres are placed into a solution of PLL. After washing, the microsphere is then added to a solution containing alginate, followed again by washing. A calcium chelator then dissolves the alginate interior of the microcapsule, and microcapsules with wall thicknesses on the order of microns result. A simple mass balance leads to the conclusion that a significant mass of PLL must be localized to the microsphere surface during the adsorption step, if it is assumed that the polymers do not self-associate. This amount of PLL could be localized to the surface of the alginate microsphere if the PLL were either to diffuse a certain distance into the alginate microsphere during the adsorption step, or if a PLL rich, viscous surface layer formed, which resisted washing, and which then gelled upon addition of alginate.

With PLL and alginate multilayers, the thickness of the formed multilayer structures was found to be a function of how well the surface was washed during multilayer formation, and the concentration of polymer. The thickness of polymer on an $Si/SiO_2$ substrate following multilayer formation was measured using ellipsometry. Thorough washing of substrates led to per layer growth on the order of tens of angstroms. However, in the specific case of 1% PLL and 1.5% alginate, less vigorous washing led to the growth of macroscopic hydrogels, with dry polymer thicknesses on the order of hundreds of angstroms per layer (See Table 3). All treated substrates became much more hydrophilic after the adsorption of the second polymer layer, and remained transparent after drying.

Ellipsometry was used to measure the effect of washing conditions on the ultimate thickness of polyelectrolyte multilayer assemblies. Less vigorous washing using the PLL/alginate polyelectrolytes led to an order of magnitude increase in the thickness of polymer on the substrate.

TABLE 3

Thickness of PLL/Alginate Layers

| Treatment | Thickness (A) ± Std. Dev. |
|---|---|
| Oxide layer | 22.9 ± 1.6 |
| 1% PLL, 1.5% alg (15 min treatment, 1 min PBS wash) × 2 | 801.6 ± 223.4 |
| 1% PLL, 1.5% alg (15 min treatment, 30 sec wash in running water) × 2 | 43.9 ± 1.4 |
| 0.1% PLL, 0.15% alg (5 min treatment, 1 min PBS wash) × 2 | 80.6 ± 8.2 |
| 2% PEI, 2% PAA (15 min, 1 min PBS wash) × 2 | 89.8 ± 11.5 |
| 2% PEI, 2% PAA (2 min, 3 × 1 min PBS wash) × 2 | 59.9 ± 8.8 |

"Thick" multilayer structures can be formed which are clear and transparent. When 1.4% alginate is placed into a small well, and 1% PLL is layered on top, a clear complex gel forms at the interface, which can be removed from the well with a spatula. However, layering of 0.1% PLL on top of 1.4% alginate does not yield a gel, only a precipitate. Substitution of PEI for PLL also leads only to the formation of a precipitate with 1.4% alginate. Layering of 2% PEI onto 2% PAA 50K does not lead to complex gel formation, however, layering 2% PEI onto 25% PAA 50K at pH 3, leads to the formation of a clear gel. Thus, by the proper choice of viscosities and charge densities, three dimensional gels can be formed upon mixing of polyelectrolytes, as opposed to the formation of a simple precipitate or flocculate. The results are summarized in Table 4.

TABLE 4

Effect of Various Treatments on the Formation of PLL/alginate layers

| Treatment | Polymers | Result |
|---|---|---|
| Direct mixing | 1.4% alg, 1% PLL | Precipitate only |
|  | 1.4% alg, 0.05% PLL | Precipitate only |
|  | 2% PAA, 2% PEI | Precipitate only |
|  | 25% PAA, 2% PEI | Precipitate only |
| Layering a solution of a polycation onto a solution of a polyanion | 1.4% alg, 1% PLL | Clear gel |
|  | 1.4% alg, 0.1% PLL | Precipitate only |
|  | 1.4% alg, 2% PEI | Precipitate only |
|  | 1.4% alg, 1% PEI | Precipitate only |
|  | 2% PAA, 2% PEI | Precipitate only |
|  | 2% PAA, 1% PLL | Precipitate only |
|  | 25% PAA (pH 3), 2% PEI | Clear gel, with cloudy edges |
|  | 25% PAA (pH 7), 2% PEI | Cloudy gel |
|  | 25% PAA, 50% PEI | Slightly cloudy gel |

HFF ECM, Treated with "Thick Multilayers"

Conditions which lead to the formation of "thick" multilayers, as judged by ellipsometry, yield very thin, clear, transparent surface films on substrates, which can be seen microscopically, and which can be pealed away from the substrate with a spatula (demonstrating significant horizontal mechanical integrity), but folding in on itself as it is pulled away from the surface, forming an opaque mass.

Using 1% PLL and 1.5% alginate, with 15 min incubation times, with one PBS wash following each adsorption step, multilayers were formed onto the HFF ECM surface, and cell adhesion to the substrates

TABLE 5

Number of Spread Cells on Polyelectrolyte Layers

| Treatment | | Number of Spread Cells/mm$^2$ (± S.D.) |
|---|---|---|
| 1% PLL/1.5% alg | 0 layers | Monolayer |
|  | 1 layer | 0 ± 0 |
|  | 2 layers | 0 ± 0 |
| 2% PEI/2% PAA | 0 layers | Monolayer |
|  | 1 layers | Monolayer |
|  | 2 layers | Monolayer |

EXAMPLE 6

Cell Spreading on a Silicon Dioxide Surface

Cell spreading is indicative of protein adsorption on a surface. Various comb copolymers were applied to a silicon oxide surface and cell spreading on the coated surfaces was evaluated. The polymers were PLL-g-PEG comb copolymers, with the ratios of PEG to lysine units as shown below in Table 1. As shown in Table 1, coating the surface with various polymeric materials is able to prevent cell spreading, and can therefore prevent protein adsorption.

TABLE 6

Cell Spreading on a SiO$_2$ Surface

| Copolymer | Number of spread cells (cell/mm$^2$) |
|---|---|
| PLL | 98 ± 27 |
| PLL-g-PEG (PEG MW | 1 ± 1 |

TABLE 6-continued

Cell Spreading on a SiO$_2$ Surface

| Copolymer | Number of spread cells (cell/mm$^2$) |
|---|---|
| 5000, PLL MW 20,000, 1 PEG per 14 lysine units) | |
| PLL-g-PEG (PEG MW 5000, PLL MW 20,000, 1 PEG per 10.5 lysine units) | 0.4 ± 0.7 |
| PLL-g-PEG (PEG MW 5000, PLL MW 20,000, 1 PEG per 7 lysine units) | 3 ± 5 |
| PLL-g-PEG (PEG MW 5000, PLL MW 20,000, 1 PEG per 3.5 lysine units) | 0 ± 0 |
| PLL-g-PEG (PEG MW 5000, PLL MW 20,000, 1 PEG per 1.75 lysine units) | 190 ± 156 |
| PEG | 157 ± 70 |

As shown in Table 6, PEG/PLL polymers with specific graft ratios of PEG per lysine subunits were able to prevent cell spreading, whereas other PEG/PLL polymers with different graft ratios were ineffective.

EXAMPLE 7

Cell Spreading on Multilayer Films

Peptides were attached via their N-terminal amines to the carboxyl side chains of polyacrylic acid (MW 250,000) (PAA) with N,N,N',N'-tetramethyluronium tetrafluoroborate (TSTU). Activated PAA was prepared by combining 200 µl of 20 mg/ml PAA in anhydrous DMF with 40 µl of 50 mg/ml TSTU and 20 µl of di-isopropyl ethylamine (DIPEA) to achieve a mixture with 61 µmol PAA COOH moieties, 6.7 µmol TSTU and 121 µmol DIPEA. A solution of peptide in buffer was added dropwise to the activated PAA. The peptide-PAA crude mixture was purified of unbound peptides by dialysis. The samples were lyophilized. This process was performed as described with the Arg-Gly-Asp (RGD-), Arg-Asp-Gly (RDG-), Tyr-Ile-Gly-Ser-Arg (YIGSR-), an His-Ala-Val (HAV-) containing peptides.

Polyelectrolyte multilayers were made within the wells of 24-well tissue culture polystyrene dishes by adsorbing alternating layers of polyethylene imine (MW 50,000) (PEI) and PAA or peptide-PAA. The first layer of PEI was deposited by adding 0.4 ml PEI (20 mg/ml) in pH 10.0 HEPES buffer to a well. After 2 minutes, the well was rinsed three times with 0.5 ml PBS for two minutes each rinse. The second layer was deposited by adding 0.4 ml of PAA (20 mg/ml) in pH 10.0 PBS. The well was rinsed and a second layer of PEI was deposited and rinsed as described above. The final layer was deposited by adding 200 µl of PBS plus 0.1 µmol of peptide-PAA (where the peptide-PAA concentrations are described in terms of the amount of peptide) or PAA in 30 µl of deionized water. After 30 minutes, 0.4 ml of PAA (20 mg/ml) was added and the wells were rinsed after 5 minutes.

Fibroblast cells were seeded onto polyelectrolyte multilayers at a density of 1000 cells/ml$^2$. After 14 hours incubation, the multilayer with the top layer of PAA attached to the RGD peptide led to 12,500±1500 spread cells/cm$^2$, while the control (non-sense peptide peptide RGD attached to PAA led to 2500±500 spread cells cm$^2$. The data demonstrates that peptides can be placed on the surface of a polyelectrolyte multilayer assembly.

We claim:

1. A medical device or implant formed of a material with a net anionic surface, wherein the material is selected from the group consisting of ceramic and polymer having a surface coating adsorbed thereto comprising a block copolymer comprising a polycanonic block comprising either a linear polycationic block or a dendritic polycationic block with a molecular weight sufficient to provide at least eight cationic charges, and at least one non-tissue binding block, wherein the block copolymer is applied to the surface to form a coating by ionic binding of the cationic charges to the surface, and wherein the non-tissue binding block prevents or minimizes the attachment of proteins or cells to the surface.

2. The implant or device of claim 1, wherein the non-tissue-binding block has a molecular weight in excess of 5,000 daltons.

3. The implant or device of claim 1, wherein the non-tissue-binding block has a molecular weight in excess of 50,000 daltons.

4. The implant or device of claim 1, wherein the non-tissue-binding block is selected from the group consisting of polyethylene glycol, mixed polyalkylene oxides having a solubility of at least one gram/liter in aqueous solutions, neutral water-soluble polysaccharides, polyvinyl alcohol, poly-N-vinyl pyrrolidone, non-cationic poly(meth)acrylates and combinations thereof.

5. The implant or device of claim 1, wherein the non-tissue-binding block comprises polyethylene glycol.

6. The implant or device of claim 1, wherein the polycationic block is selected from the group consisting of natural and unnatural polyamino acids having net positive charge at neutral pH, positively charged polysaccharides, and positively charged synthetic polymers.

7. The implant or device of claim 6, wherein the positively charged polysaccharide is selected from the group consisting of chitosan, partially deacetylated chitin, and amine-containing derivatives of neutral polysaccharides.

8. The implant or device of claim 6, wherein the positively charged synthetic polymer is selected from the group consisting of polyethyleneimine, polyamino(meth)acrylate, polyaminostyrene, polyaminoethylene, poly(aminoethyl) ethylene, polyaminoethylstyrene, and N-alkyl derivatives thereof.

9. The implant or device of claim 1, wherein the polycationic block comprises monomeric units selected from the group consisting of lysine, histidine, arginine and ornithine.

10. The implant or device of claim 1, wherein the copolymer further comprises a bioactive agent.

11. The implant or device of claim 10, it wherein the bioactive agent is chemically coupled to the copolymer.

12. The implant or device of claim 1, wherein the surface is ceramic.

13. The implant or device of claim 1, wherein the surface is net anionic at physiological pH.

14. A method for coating the surface of a medical device or implant formed of a material with a net anionic surface, wherein the material is selected from the group consisting of ceramic and polymer, comprising adsorbing to the surface of the medical device or implant a block copolymer, wherein:

the block copolymer includes a polycationic block comprising either a linear polycationic block or a dendritic polycationic block with a molecular weight sufficient to provide at least eight cationic charges and at least one non-tissue binding block, wherein the block copolymer is applied to the surface to form a coating by ionic binding of the cationic charges to the surface, and wherein the non-tissue binding block prevents or minimizes the attachment of proteins or cells to the surface.

15. The method of claim 14, wherein the surface is net anionic at physiological pH.

16. The method of claim 14, wherein the copolymer is applied to the surface by placing the medical device or implant in a solution containing the copolymer.

* * * * *

UNITED STATES PATENT AND TRADEMARK OFFICE
CERTIFICATE OF CORRECTION

| | | |
|---|---|---|
| PATENT NO. | : 6,743,521 B2 | Page 1 of 1 |
| APPLICATION NO. | : 09/403428 | |
| DATED | : June 1, 2004 | |
| INVENTOR(S) | : Jeffrey A. Hubbell, Donald L. Elbert and Curtis B. Herbert | |

It is certified that error appears in the above-identified patent and that said Letters Patent is hereby corrected as shown below:

Claim 11, column 26, line 6, delete "it".

Signed and Sealed this

Twenty-fourth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,743,521 B2 | Page 1 of 1 |
| APPLICATION NO. | : 09/403428 | |
| DATED | : June 1, 2004 | |
| INVENTOR(S) | : Jeffrey A. Hubbell, Donald L. Elbert and Curtis B. Herbert | |

It is certified that error appears in the above-identified patent and that said Letters Patent is hereby corrected as shown below:

Claim 11, column 24, line 6, delete "it".

This certificate supersedes the Certificate of Correction issued February 24, 2009.

Signed and Sealed this

Thirty-first Day of March, 2009

JOHN DOLL
*Acting Director of the United States Patent and Trademark Office*